United States Patent [19]

Collins et al.

[11] Patent Number: 4,689,419

[45] Date of Patent: Aug. 25, 1987

[54] NOVEL INTERMEDIATE COMPOUNDS IN A PROCESS FOR PRODUCING 16-PHENOXY- AND 16-SUBSTITUTED PHENOXY-9-KETO-PROSTATRIENOIC ACID DERIVATIVES

[75] Inventors: Paul W. Collins, Deerfield; Richard M. Weier, Lake Bluff, both of Ill.

[73] Assignee: G. D. Searle & Co., Chicago, Ill.

[21] Appl. No.: 930,616

[22] Filed: Nov. 14, 1986

[51] Int. Cl.[4] ............................................... C07F 7/18
[52] U.S. Cl. ....................................... 556/437; 556/422; 556/423; 556/427; 556/444; 549/214
[58] Field of Search ............... 556/444, 437, 427, 422, 556/423; 549/214

[56] References Cited

U.S. PATENT DOCUMENTS

| 3,985,791 | 10/1976 | Muchowski | 260/473 |
| 4,085,272 | 4/1978 | Weiss et al. | 556/437 X |
| 4,152,524 | 5/1979 | Schaub et al. | 556/437 X |
| 4,178,457 | 12/1979 | Van Horn | 560/53 |
| 4,243,817 | 1/1981 | Wissner et al. | 556/437 X |
| 4,410,720 | 10/1983 | Holland et al. | 556/437 X |
| 4,529,812 | 7/1985 | Collins | 560/121 |

FOREIGN PATENT DOCUMENTS 0146935 7/1985 European Pat. Off. ............. 560/53

OTHER PUBLICATIONS

Lambert et al., "The Tricyclo[5.1.0.0$^{3,5}$]octan-2-ols," *J. Org. Chem.*, 36, 2941–2947, (1971).

*Primary Examiner*—Paul F. Shaver
*Attorney, Agent, or Firm*—Richard E. L. Henderson; Paul D. Matukaitis

[57] ABSTRACT

This invention relates to the production of novel intermediate compounds which are useful in the process for producing 16-phenoxy- and 16-substituted phenoxy-9-keto-prostatrienoic acid derivatives, the antisecretory agents of U.S. Pat. No. 4,178,457.

12 Claims, No Drawings

NOVEL INTERMEDIATE COMPOUNDS IN A PROCESS FOR PRODUCING 16-PHENOXY- AND 16-SUBSTITUTED PHENOXY-9-KETO-PROSTATRIENOIC ACID DERIVATIVES

BACKGROUND OF THE INVENTION (1) Field of the Invention

This invention relates to novel intermediate compounds which are useful for synthesizing 16-phenoxy- and 16-substituted phenoxy-9-keto-prostatrienoic acid derivatives. These prostatrienoic acid derivatives are the subject matter of U.S. Pat. No. 4,178,457. Because the 16-phenoxy- and 16-substituted phenoxy-9-keto-prostatrienoic acid derivatives possess antisecretory activity, they are useful as inhibitors of gastric acid secretion in mammals.

(2) Description of the Related Art

Muchowski, U.S. Pat. No. 3,985,791, describes the invention of 16-phenoxy- and 16-(o, m, or p)-substituted phenoxy derivatives of 9α,11α,15-trihydroxy-17,18,19,20-tetranorprosta-4,5,13-trans-trienoic acids and a multistep process for the production of these compounds. Because the compounds described by Muchowski contained a hydroxyl group at the C-9 and C-11 positions they are classified as belonging to the PGF series.

Van Horn, U.S. Pat. No. 4,178,457, describes the invention of (dl)-16-phenoxy- and 16-substituted phenoxy-9-keto-prostatrienoic acid derivatives and the process for producing them. Van Horn's compounds are merely the 9-keto analogues of the compounds of the Muchowski invention. Van Horn's process is a 3-step process consisting of protecting the 11α and 15 hydroxyl groups of the Muchowski compounds, whereupon Van Horn was able to selectively oxidize the 9-hydroxyl group to a 9-keto group. Thereafter, he removed the protecting groups to produce the compounds of the invention. By converting the 9-hydroxyl group of the Muchowski compounds to a 9-keto group, Van Horn converted the prostaglandin derivatives from the series designated as PGF to the series designated as PGE.

Syntex, European Patent Publication No. 0146935, describes the multistep process for making 16-phenoxy- and 16-substituted phenoxy-prostatrienoic acid esters. At page 2, line 5, Syntex identifies, as twin problems in the process of producing the aforementioned compounds, the problems of how to prepare an individual stereoisomer of the subject compounds while allowing an initial selective deprotection of the C-9 hydroxyl group so that it can be oxidized to the 9-keto functionality without also oxidizing the C-11 and C-15 groups and yet allowing the subsequent deprotection of C-11 and C-15 without degrading the resulting molecule.

Syntex's approach to the problem of selective deprotection of the C-9 hydroxyl group is to employ a base labile ether forming group such as trialkylsilyl at the C-9 hydroxyl, and a base-stable acid-labile ether forming group such as tetrahydropyranyl at the C-11 and C-15 hydroxyls.

The present invention differs from the Syntex invention in that the present invention precludes the need to selectively oxidize the C-9 hydroxyl group late in the process. Specifically, the present invention builds upon 2-(2-propynyl)-4-(triethylsilyloxy)-2-cyclopenten-1-one (U.S. Pat. No. 4,529,812), a compound which already possesses the keto group at the C-9 position and which retains the keto group on the cyclopentyl ring in enol form, thereby avoiding the steps of selective protection, deprotection, and oxidation of the C-9 hydroxyl group described by Syntex.

Moreover, the present invention differs from the Syntex invention because it precludes the need for chain extension chemistry. Specifically, the present invention precludes the need for steps 9–13 on pages 12 and 13 of European Patent Publication No. 0146935 (Syntex).

Overall, the present invention provides a more efficient route to producing 16-phenoxy- and 16-substituted phenoxy-9-keto-prostatrienoic acid derivatives than has previously been described.

SUMMARY OF THE INVENTION

This invention relates to novel compounds of the formulas:

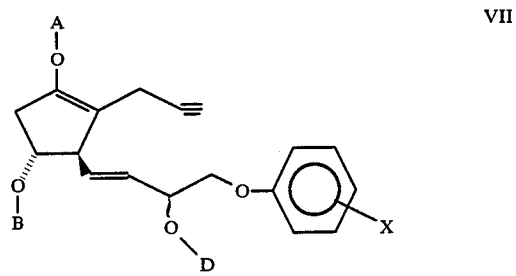

VII

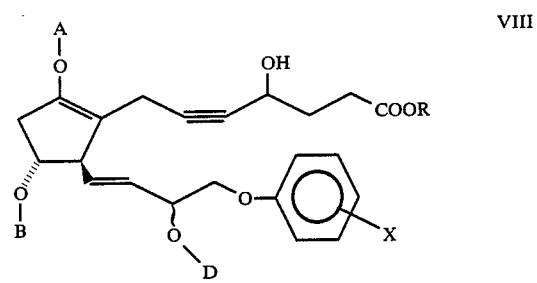

VIII

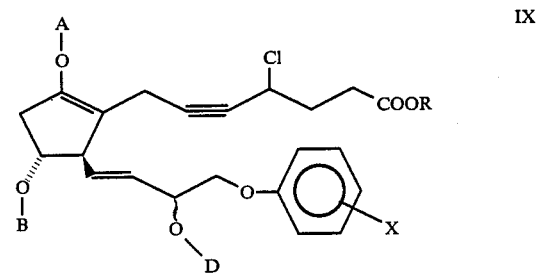

IX

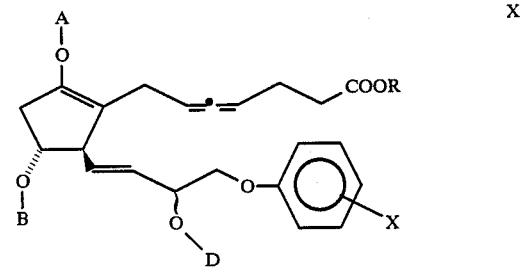

X wherein X is selected from the group consisting of hydrogen, lower alkyl having 1–6 carbon atoms, —OR″, —SR″, —NR″₂, Cl, Br, F, —NO₂, and —CF₃; wherein R″ represents lower alkyl having 1–6 carbon atoms or —SiR$^1$R$^2$R$^3$, wherein R$^1$, R$^2$, and R$^3$ are the same or different and are lower alkyl of 1–6 carbon atoms or phenyl;

wherein R represents lower alkyl having 1–6 carbon atoms or —SiR$^1$R$^2$R$^3$, wherein R$^1$, R$^2$, and R$^3$ are the same or different and are lower alkyl of 1–6 carbon atoms or phenyl;

wherein A represents an enolate ion trapping group, preferably SiR$^1$R$^2$R$^3$, wherein R$^1$, R$^2$, and R$^3$ are the same or different and are lower alkyl of 1–6 carbon atoms or phenyl;

wherein B and D represent ether forming groups such as tetrahydropyranyl, tetrahydrofuranyl, trialkylsilyl, triphenylsilyl, and the like, preferably SiR$^1$R$^2$R$^3$, wherein R$^1$, R$^2$, and R$^3$ *are the same or different and are lower alkyl of* 1–6 carbon atoms or phenyl.

The compounds of the invention are useful because they are intermediate compounds in a novel process for producing 16-phenoxy- and 16-substituted phenoxy-9-keto-prostatrienoic acid derivatives. These latter compounds, which are the antisecretory agents of U.S. Pat. No. 4,178,457, are particularly useful in inhibiting gastric secretion in mammals.

DETAILED DESCRIPTION OF THE INVENTION

The invention encompasses compounds of Formulas VII, VIII, IX, and X which are novel intermediates in a novel process for producing 16-phenoxy- and 16-substituted phenoxy-9-keto-prostatrienoic acid derivatives. Because the compounds of the invention are prostaglandin analogues, the numbering system used in the discussion is based upon the numbering system assigned to the prostanoic acid skeleton:

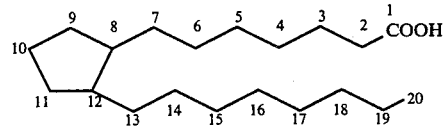

For example, by referring to the numbering used in the prostanoic acid skeleton, the keto group on the cyclopentenone ring of the compound of Formula VI would be discussed as being the keto group at C-9 for the prostaglandin analogues which are the subject matter of this invention.

The novel compounds of the present invention can be obtained by a process illustrated by the following sequence of reactions:

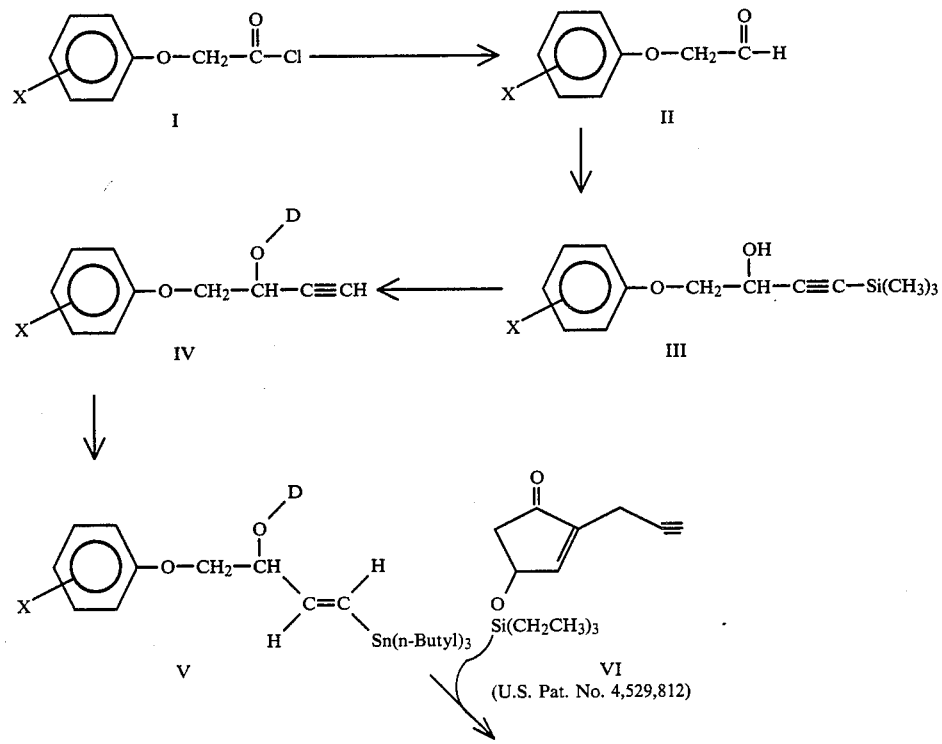

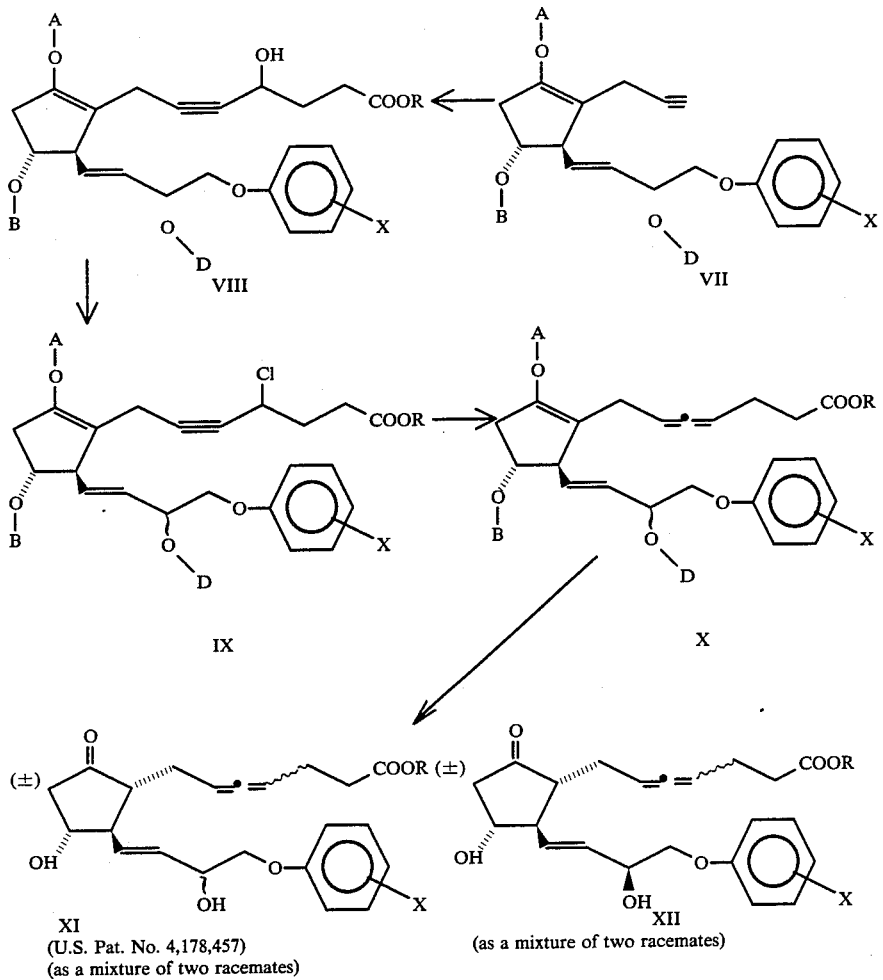

wherein X is selected from the group consisting of hydrogen, lower alkyl having 1-6 carbon atoms, —OR″, —SR″, —NR″₂, Cl, Br, F, —NO₂, and —CF₃; wherein R″ represents lower alkyl having 1-6 carbon atoms;

wherein R represents lower alkyl having 1-6 carbon atoms;

wherein B and D represent ether forming groups such as tetrahydrofuranyl, tetrahydropyranyl, or trialkyl- or triphenylsilyl; and wherein A represents an enolate ion trapping group, such as trialkyl-, dialkylphenyl-, diphenylalkyl-, or triphenylsilyl.

The starting material represented by Formula I is commercially available. In the reaction sequence, the compound of Formula I is reduced by hydrogenation at room temperature and under low hydrogen pressure such as 5 p.s.i. using 10% palladium on carbon in a solvent such as tetrahydrofuran containing 2,6-dimethylpyridine.

The compound of Formula II is then acetylenated, by treatment with trimethylsilylacetylene in the presence of a strong base such as n-butyl lithium, in an aprotic solvent such as tetrahydrofuran (THF), at a reduced temperature of about −20° C. The resulting reaction mixture is allowed to come to 0° and is complete in 4 hours.

The silylacetylene compound of Formula III is first desilylated at the acetylene and then silylated at the hydroxy to form the silyloxy compound of Formula IV by initially treating the compound of Formula III at room temperature for about 2 hours with potassium fluoride in a solvent such as dimethylformamide (DMF) in the presence of water; and then by subsequently treating the reaction mixture overnight with a trialkylchlorosilane or triphenylchlorosilane, preferably triethylchlorosilane, in a polar solvent such as DMF, in the presence of imidazole at ambient temperature.

The compound of Formula IV is then hydrostannated in a free radical reaction by treatment with a trialkylstannane, preferably tributylstannane, in the presence of ultraviolet light such as from a sunlamp, in an inert atmosphere such as argon, and at a temperature maintained at ambient. Due to the nature of the free radical addition to the triple bond, the resulting compound of Formula V will have a trans double bond that will become the C-13 trans double bond of compound XI, analogous to the C-13 trans double bond present in naturally occurring prostaglandin compounds and in the compounds of U.S. Pat. No. 4,178,457.

The compound of Formula V is added to the double bond of the compound of Formula VI by means of a nucleophilic conjugate addition. The cuprate nucleophile is generated by reacting the compound of Formula V sequentially with a strong base such as n-butyl lithium in an aprotic solvent such as THF, followed by copper-1-pentyne and hexamethylphosphorous triamide. The addition occurs when the compound of Formula VI is added dropwise to the reaction mixture. In order to retain the resulting enol form, the reaction mixture is treated with an enolate ion trapping group such as a trialkylchlorosilane, dialkylphenylchlorosilane, diphenylalkylchlorosilane, or triphenylchlorosilane, preferably t-butyldimethylchlorosilane, to produce the enol ether of Formula VII. On compound VI, the size of the silyloxy group on the carbon adjacent to the double bond causes addition to the double bond to occur on the side opposite the silyloxy group, producing a mixture of two racemates. However, for the sake of clarity, only the racemate possessing the 11α-silyloxy and 12β-side chain is depicted in the reaction sequence. Compound VI in the above sequence is prepared as described in U.S. Pat. No. 4,529,812.

The acetylene group of the compound of Formula VII is converted into a nucleophile by treatment with a strong base such as N-butyl lithium in an aprotic solvent such as THF, at $-60°$ C., under an inert atmosphere such as argon. The resultant nucleophile is subsequently reacted with methyl 3-formyl-propanoate for about 30 minutes at low temperature, preferably $-60°$ C., to form the addition product of Formula VIII.

Alternatively, the acetylide anion may be quenched with a trialkylsilyl ether of 3-formyl propanoic acid, $OHCCH_2CH_2-CO_2R$, where $R=SiR^1R^2R^3$ and $R^1$, $R^2$, and $R^3$ are the same or different and are lower alkyl of 1-6 carbon atoms or phenyl.

The 4-hydroxy group of the compound of Formula VIII is substituted by a chloro group to produce the compound of Formula IX by initially treating the compound of Formula VIII with $CCl_4$ and triethylamine in an inert solvent such as diethyl ether, at 0° C., under an inert atmosphere such as argon; and by subsequently treating the resulting reaction mixture with hexamethylphosphorous triamide for about 1.25 hours at 0° C.

The chloroacetylene compound of Formula IX is converted to the allene compound of Formula X by treatment for about 30 minutes with a zinc-copper couple, prepared according to the procedure of Lambert et al., *J. Org. Chem.*, 36, 2941 (1971), in a protic solvent such as ethanol, in the presence of an acid catalyst such as glacial acetic acid and under an inert atmosphere such as nitrogen.

The compound of Formula X is simultaneously desilylated at three different positions and the resulting en-9-ol is converted to a 9-keto group in a single step by treating the compound of Formula X with an organic acid, such as acetic acid, in THF to facilitate dissolution and in the presence of water, with stirring overnight. Following chromatographic separation from diastereomeric racemates, the resulting compound of Formula XI is obtained as a mixture of two racemates and is the subject matter of U.S. Pat. No. 4,178,457. The other pair of diastereomers is represented as Formula XII in the reaction sequence.

By utilizing optically active starting materials, this process is amenable to producing single stereoisomers as well. Specifically, one could resolve the cyclopentenone compound of Formula VI and the side chain intermediate of Formula IV using known technology. By employing the proper isomers in the above reaction sequence, one skilled in the art could produce the compound of Formula XI or XII exhibiting the desired stereochemistry.

DESCRIPTION OF THE MOST PREFERRED EMBODIMENTS

These examples are given by way of illustration only and are not to be construed as limiting the invention either in spirit or in scope as many modifications in materials and methods will be apparent from this disclosure to those skilled in the art.

EXAMPLE 1

Phenoxyacetyl chloride (9.3 g) in 100 ml of THF was hydrogenated over 10% palladium on carbon in the presence of 5.85 g of 2,6-dimethylpyridine at room temperature and 5 p.s.i. pressure. The resulting solution was evaporated under reduced pressure and the residue was dissolved in ether. The ether containing the residue was successively washed with 1N HCl, $H_2O$, dilute potassium carbonate solution, and $H_2O$. The organic layer was separated, dried ($Na_2SO_4$) and evaporated to produce 5.3 g of a semisolid residue containing phenoxyacetaldehyde (II), which was used directly in the next step without further purification.

EXAMPLE 2

To 7.2 g of trimethylsilylacetylene dissolved in 110 ml of THF and cooled to $-20°$ C. was added 46.2 ml of 1.55M n-butyl lithium in hexane. The mixture was allowed to come to room temperature for 15 minutes, recooled to $-20°$ C., and treated dropwise with 5.3 g of phenoxyacetaldehyde (II) in THF. After the addition was complete, the reaction mixture was stirred at 0° C. for 4 hours. The reaction mixture was then poured into a mixture of ether:hexane (1:1) over 0.5N HCl and shaken. The organic layer was separated, washed 3 times with $H_2O$, dried ($Na_2SO_4$), and evaporated to dryness. The residue was chromatographed on a column of silica gel that was eluted with 30% ethyl acetate in hexane to yield 3.8 g of 1-phenoxy-4-trimethylsilyl-but-3-yn-2-ol (III).

EXAMPLE 3

A mixture containing 3.8 g of 1-phenoxy-4-trimethylsilylbut-3-yn-2-ol (III), 3.8 g of potassium fluoride, and 1 ml of $H_2O$ in 30 ml of DMF was stirred at room temperture for about 2 hours. The above mixture was then diluted with ether and washed 4 times with $H_2O$. The organic layer was separated, dried ($Na_2SO_4$) and evaporated under reduced pressure to produce 2.7 g of residue. To the entire residue dissolved in 25 ml of DMF was added 2 g of triethylchlorosilane and 1.5 g of imidazole. The reaction mixture was allowed to stir overnight at room temperature. The reaction mixture was then diluted with ether:hexane (1:1), washed 3 times with water, separated from the aqueous layer, dried ($Na_2SO_4$) and evaporated to produce a residue. The residue was chromatographed on a silica gel column that was eluted with 5% ethyl acetate in hexane to produce 2.3 g of 2-triethylsilyloxy-1-phenoxybut-3-yne (IV).

EXAMPLE 4

A mixture of 2.3 g of 2-triethylsilyloxy-1-phenoxybut-3-yne (IV) and 2.52 g of tributylstannane were stirred for 2 hours under argon while being irradiated with a sunlamp, the reaction vessel being kept in a water bath to maintain the reaction mixture at room temperature.

EXAMPLE 5

To 4.82 g of the product from Example 4 containing the 2-triethylsilyloxy-1-phenoxy-4-(tri-n-butylstannyl)-but-3-transene (V) dissolved in 15 ml of dry THF and cooled to $-60°$ C. under argon was added 5.7 ml of 1.55M n-butyl lithium in hexane. After 30 minutes, a solution of 1.15 g of copper-1-pentyne and 2.82 of hexamethylphosphorous triamide in about 15 ml of ether was added. After 10 minutes, a solution of 1.75 g of 2-(2-propynyl)-4-(triethylsilyloxy)-2-cyclopenten-1-one (VI), (U.S. Pat. No. 4,529,812), in 10 ml of ether was added. After 30 minutes, 17 ml of hexamethylphosphoric triamide and a solution of 1.32 g of t-butyldimethylchlorosilane in 5 ml of ether were added to the reaction mixture and the temperature was allowed to rise to $-20°$ C. and maintained there for about an hour. The reaction mixture was then diluted with ether and washed 1 time with 0.5N HCl and 3 times with $H_2O$. The organic layer was separated, dried ($Na_2SO_4$), and evaporated. The residue was chromatographed on a column of silica gel and eluted with 2.5% ethyl acetate in hexane to produce 4.2 g of 2-(propynyl)-1-(t-butyldimethylsilyloxy)-3-(4-phenoxy-3-triethylsilyloxybut-1-enyl)-1-cyclopentene (VII) having the following physical characteristics:

NMR $\delta_{TMS}{}^{CDCl_3}$(80 MHz): 1.83 (t, C≡C—H); 4.0 (m, C-11); 5.6 (m, C-13 and C-14); 7.0 (m, aromatic protons).

EXAMPLE 6

To 642 mg of 2-(propynyl)-1-(t-butyldimethylsilyloxy)-4-(triethylsilyloxy)-3-(4-phenoxy-3-triethylsilyloxybut-1-enyl)-1-cyclopentene (VII) dissolved in 8 ml of dry THF and cooled to $-60°$ C. under argon was added 0.83 ml of 1.55M n-butyl lithium in hexane. The reaction mixture was stirred at $-20°$ C. for about 30 minutes, recooled at $-60°$ C., and then treated with a solution of 348 mg of methyl 3-formylpropanoate in 2 ml of THF. The reaction mixture was stirred for about 30 minutes at $-60°$ C., then poured into a 1:1:1 mixture of ether, hexane, and 0.5N HCl. The organic layer was separated, washed two times with $H_2O$, dried ($Na_2SO_4$), and evaporated under reduced pressure. The residue was chromatographed on a silica gel column that was eluted with 12% ethyl acetate in hexane to yield 462 mg of (dl)-4-hydroxy-9-t-butyldimethylsilyloxy-11α,15-bis-triethylsilyloxy-16-phenoxy-17,18,19,20-tetranorprosta-5-yn-8,13-trans-dienoic acid methyl ester (VIII).

NMR $\delta_{TMS}{}^{CDCl_3}$(80 MHz): 3.62 (s, OCH₃); 3.83 (d, C-16); 4.00 (m, C-11); 4.4 (m, C-4 and C-15).

EXAMPLE 7

To a solution of 155 mg (0.20 mmol) of (dl)-4-hydroxy-9-t-butyldimethylsilyloxy-11α,15-bis-triethylsilyloxy-16-phenoxy-17,18,19,20-tetranorprosta-5-yn-8,13-trans-dienoic acid methyl ester (VIII), 32 mg (0.32 mmol) of triethylamine, and 155 mg (1.01 mmol) of carbon tetrachloride in 8 ml of diethyl ether at 0° C. was added 102 mg (0.62 mmol) of hexamethylphosphorous triamide in ether over 15 minute period with stirring under argon. The stirring at 0° C. under argon was continued for 1.25 hours when TLC (20% ethyl acetate/hexane) showed the reaction to be complete. The reaction mixture was poured onto a saturated sodium chloride solution and extracted 3 times with diethyl ether. The combined ether layers were washed twice with a saturated sodium chloride solution, separated, and dried over $Na_2SO_4$. The organic layer was filtered and the solvent was removed from the filtrate under reduced pressure. The resultant oil was combined with the crude oil obtained from a similar chlorination reaction employing 60 mg of (VIII) and chromatographed on a silica gel column that was eluted with mixtures of ethyl acetate in hexane to yield 166 mg of (dl)-4-chloro-9-t-butyldimethylsilyloxy-11α-15-bis-triethylsilyloxy-16-phenoxy-17,18,19,20-tetranorprosta-5-yn-8,13-trans-dienoic acid methyl ester (IX) having the following physical constants:

NMR $\delta_{TMS}{}^{CDCl_3}$(80 MHz): 3.65 (s, 3H, OCH₃), 3.84 (d, 2H, J=7 Hz, C-16); 4.00 (m, 1H, C-11); 4.53 (m, 2H, C-4 and C-15); 5.6 (m, 2H, C-13 and C-14).

EXAMPLE 8

To a stirred solution of 101 mg (0.13 mmol) of (dl)-4-chloro-9-t-butyldimethylsilyloxy-11α-15-bis-triethylsilyloxy-16-phenoxy-17,18,19,20-tetranorprosta-5-yne-8,13-trans-dienoic acid methyl ester (IX) in 7 ml of absolute ethanol at room temperature under nitrogen was added 101 mg of Zn/Cu couple, prepared by the method of Lambert et al., *J. Org. Chem.*, 36 2941 (1971).

Reduction did not occur until 40 mg of glacial acetic acid was added, the reduction becoming complete within 30 minutes. The reaction mixture was filtered and the solvent evaporated under reduced pressure to give a gummy crude product. The gummy product was extracted with hexane, filtered and stripped in vacuo. The residue was combined with the crude product from a similar reaction that employed 58 mg of (IX) as the starting material. The combined products were chromatographed on a column of silica gel which was eluted with mixtures of ethyl acetate and hexane to give 113 mg of (dl)-9-t-butyldimethylsilyloxy-11α,15-bis-triethylsilyloxy-16-phenoxy-17,18,19,20-tetranorprosta-4,5,8,13-trans-tetraenoic acid methyl ester (X).

EXAMPLE 9

A mixture containing 113 mg (0.15 mmol) of (dl)-9-t-butyldimethylsilyloxy-11α,15-bis-triethylsilyloxy-16-phenoxy-17,18,19,20-tetranorprosta-4,5,8,13-trans-tetraenoic acid methyl ester (X) and acetic acid:THF:H₂O (3:1:1) was stirred at room temperature overnight. The reaction mixture was initially heterogeneous but became homogeneous shortly after stirring began. After stirring overnight, all solvents were removed under vacuum. The residue was chromatographed on a silica gel column which was eluted with mixtures of ethyl acetate and hexane to yield 32 mg of (dl)-9-keto-11α-15-dihydroxy-16-phenoxy-17,18,19,20-tetranorprosta-4,5,13-trans-trienoic acid methyl ester (XI) as a mixture of two racemates, which was identical with authentic Enprostil, U.S. Pat. No. 4,178,457 and which had the following physical constants:

NMR $^{13}C$ ppm: 216.3, 216.2 (cyclopentanone carbonyls); 205.9, 205,8 (allene central carbons); 175.0 (ester carbonyl); 160.2, 130.4, 121.8, 115.6 (benzene ring carbons);

NMR $^1H$ $\delta_{TMS}{}^{CDCl_3}$ [200 MHz]: 3.62 (s, 3H, OCH₃); 3.94 (d, 2H, J=7 Hz, C-16); 4.12 (m, 1H, C-11); 4.47 (m, 1H, C-15); 5.09 (m, 2H, allene); 5.8 (m, 2H, C-13 and C-14);

and compound XII as a mixture of two racemates, which had the following physical constants:

NMR $^{13}C$ ppm: 216.4, 216.5 (cyclopentanone carbonyls); 205.9, 206.0 (allene central carbons); 175.1 (ester carbonyl);

NMR $^1$H $\delta_{TMS}{}^{CDCl_3}$ [200 MHz]: 3.60 (s, 3H, OCH$_3$); 4.10 (m, 1H, C-11); 4.47 (m, 1H, C-15); 5.10 (m, 2H, allene); 5.8 (m, 2H, C-13 and C-14).

What is claimed is:

1. A compound of the formula

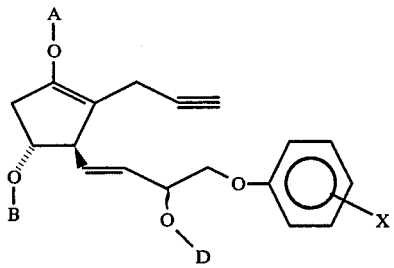

wherein X is selected from the group consisting of hydrogen, lower alkyl having 1-6 carbon atoms, —OR", —SR", —NR"$_2$, Cl, Br, F, NO$_2$, and —CF$_3$; wherein R" represents lower alkyl having 1-6 carbon atoms; wherein A represents SiR$^1$R$^2$R$^3$; wherein B and D are the same or different and are members of the group consisting of SiR$^1$R$^2$R$^3$, tetrahydropyranyl, and tetrahydrofuranyl; wherein R$^1$, R$^2$, and R$^3$ are the same or different and are lower alkyl of 1-6 carbon atoms or phenyl.

2. A compound according to claim 1 wherein A is t-butyldimethylsilyl, and wherein B and D are triethylsilyl.

3. A compound according to claim 1 wherein A is t-butyldimethylsilyl, wherein B and D are triethylsilyl and wherein X is hydrogen.

4. A compound of the formula

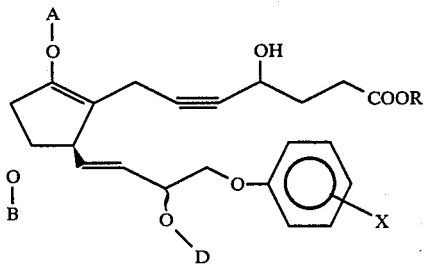

wherein X is selected from the group consisting of hydrogen, lower alkyl having 1-6 carbon atoms, —OR", —SR", —NR"$_2$, Cl, Br, F, NO$_2$, and —CF$_3$; wherein R" represents lower alkyl having 1-6 carbon atoms; wherein R represents lower alkyl having 1-6 carbon atoms; wherein A represents SiR$^1$R$^2$R$^3$; wherein B and D are the same or different and are members of the group consisting of SiR$^1$R$^2$R$^3$, tetrahydropyranyl, and tetrahydrofuranyl; and wherein R$^1$, R$^2$, and R$^3$ are the same or different and are lower alkyl of 1-6 carbon atoms or phenyl.

5. A compound according to claim 4 wherein A is t-butyldimethylsilyl, and wherein B and D are triethylsilyl.

6. A compound according to claim 4 wherein A is t-butyldimethylsilyl, wherein B and D are triethylsilyl, wherein X is hydrogen, and wherein R is methyl.

7. A compound of the formula

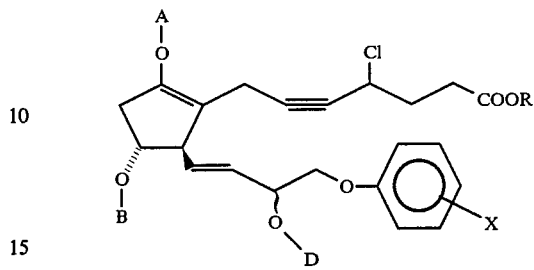

wherein X is selected from the group consisting of hydrogen, lower alkyl having 1-6 carbon atoms, —OR", —SR", —NR"$_2$, Cl, Br, F, NO$_2$, and —CF$_3$; wherein R" represents lower alkyl having 1-6 carbon atoms; wherein R represents lower alkyl having 1-6 carbon atoms; wherein A represents SiR$^1$R$^2$R$^3$; wherein B and D are the same or different and are members of the group consisting of SiR$^1$R$^2$R$^3$, tetrahydropyranyl, and tetrahydrofuranyl; and wherein R$^1$, R$^2$, and R$^3$ are the same or different and are lower alkyl of 1-6 carbon atoms or phenyl.

8. A compound according to claim 7 wherein A is t-butyldimethylsilyl, and wherein B and D are triethylsilyl.

9. A compound according to claim 7 wherein A is t-butyldimethylsilyl, wherein B and D are triethylsilyl, wherein X is hydrogen, and wherein R is methyl.

10. A compound of the formula

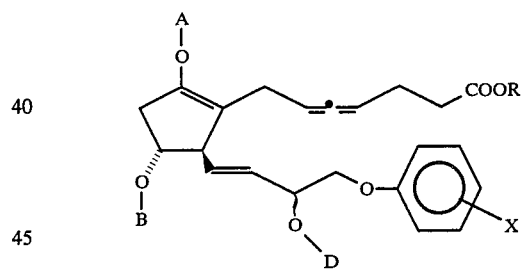

wherein X is selected from the group consisting of hydrogen, lower alkyl having 1-6 carbon atoms, —OR", —SR", —NR"$_2$, Cl, Br, F, NO$_2$, and —CF$_3$; wherein R" represents lower alkyl having 1-6 carbon atoms; wherein R represents lower alkyl having 1-6 carbon atoms; wherein A represents SiR$^1$R$^2$R$^3$; wherein B and D are the same or different and are members of the group consisting of SiR$^1$R$^2$R$^3$, tetrahydropyranyl, and tetrahydrofuranyl; and wherein R$^1$, R$^2$, and R$^3$ are the same or different and are lower alkyl of 1-6 carbon atoms or phenyl.

11. A product according to claim 10 wherein A is t-butyldimethylsilyl, and wherein B and D are triethylsilyl.

12. A compound according to claim 10 wherein A is t-butyldimethylsilyl, wherein B and D are triethylsilyl, wherein X is hydrogen, and wherein R is methyl.

* * * * *

UNITED STATES PATENT AND TRADEMARK OFFICE
CERTIFICATE OF CORRECTION

PATENT NO. : 4,689,419
DATED : August 25, 1987
INVENTOR(S) : Paul W. Collins

It is certified that error appears in the above-identified patent and that said Letters Patent are hereby corrected as shown below:

Column 5, reaction number VIII, that portion of the structure reading  should read 

Column 5, reaction number XI, that portion of the structure reading  should read 

UNITED STATES PATENT AND TRADEMARK OFFICE
CERTIFICATE OF CORRECTION

PATENT NO. : 4,689,419

DATED : August 25, 1987

INVENTOR(S) : Paul W. Collins

It is certified that error appears in the above-identified patent and that said Letters Patent is hereby corrected as shown below:

Column 6, reaction number VII, that portion of the structure reading  should read 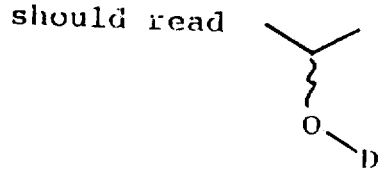

Signed and Sealed this

Thirtieth Day of August, 1988

Attest:

DONALD J. QUIGG

Attesting Officer · Commissioner of Patents and Trademarks